(12) United States Patent
Schiller et al.

(10) Patent No.: US 9,295,769 B2
(45) Date of Patent: Mar. 29, 2016

(54) DIALYSIS DEVICE

(75) Inventors: Wolfgang Schiller, Bonn (DE); Thomas Schmid, Schondorf (DE); Hiep T Nguyen, Jamaica Plain, MA (US)

(73) Assignee: DUALIS MEDTECH GMBH, Seefeld (DE)

( * ) Notice: Subject to any disclaimer, the term of this patent is extended or adjusted under 35 U.S.C. 154(b) by 99 days.

(21) Appl. No.: 14/239,417

(22) PCT Filed: Aug. 14, 2012

(86) PCT No.: PCT/EP2012/065886
§ 371 (c)(1),
(2), (4) Date: Aug. 7, 2014

(87) PCT Pub. No.: WO2013/024091
PCT Pub. Date: Feb. 21, 2013

(65) Prior Publication Data
US 2015/0112240 A1    Apr. 23, 2015

(30) Foreign Application Priority Data
Aug. 18, 2011    (DE) .......................... 10 2011 081 204

(51) Int. Cl.
*A61M 5/00*    (2006.01)
*A61M 1/16*    (2006.01)
*A61M 27/00*    (2006.01)

(52) U.S. Cl.
CPC ........... *A61M 1/1678* (2013.01); *A61M 1/1601* (2014.02); *A61M 27/002* (2013.01); *A61M 2205/04* (2013.01)

(58) Field of Classification Search
CPC ............ A61M 1/1678; A61M 1/1601; A61M 2205/04; A61M 27/002
See application file for complete search history.

(56) References Cited

U.S. PATENT DOCUMENTS

| | | | |
|---|---|---|---|
| 374,854 A | 12/1887 | Stevens | |
| 4,524,466 A | 6/1985 | Hall et al. | |
| 5,397,354 A | 3/1995 | Wilk et al. | |
| 8,398,536 B2 | 3/2013 | Vodermayer et al. | |
| 2006/0030809 A1* | 2/2006 | Barzilay ............. | A61M 1/1037 604/6.11 |

(Continued)

FOREIGN PATENT DOCUMENTS

| DE | 102006035798 A1 | 2/2008 |
|---|---|---|
| DE | 102008017448 A1 | 10/2009 |

OTHER PUBLICATIONS

International Search Report dated Feb. 28, 2013 for PCT/EP2012/065886.

(Continued)

*Primary Examiner* — Philip R Wiest
*Assistant Examiner* — Ariana Zimbouski
(74) *Attorney, Agent, or Firm* — Ohlandt, Greeley, Ruggiero & Perle, L.L.P.

(57) ABSTRACT

According to one embodiment, a dialysis device is made available that can be implanted at least partially into the body of a patient and comprises a blood chamber, through which the patient's blood can flow, a dialysis chamber for receiving a dialysate, and a hydraulic pump device for compressing the two chambers alternately by means of a hydraulic fluid, wherein both chambers are each equipped with two valves for controlling the inflow and outflow of blood and dialysate, respectively, and wherein both chambers are connected to each other in an area designed as a membrane.

8 Claims, 1 Drawing Sheet

(56) References Cited

U.S. PATENT DOCUMENTS

2009/0234266 A1* 9/2009 Solomon ............. A61M 1/1678
 604/6.09
2011/0137107 A1 6/2011 Vodermayer et al.

OTHER PUBLICATIONS

Written Opinion Report dated Feb. 28, 2013 for PCT/EP2012/065886.

* cited by examiner

DIALYSIS DEVICE

BACKGROUND

1. Field of the Disclosure

The disclosure generally relates to a dialysis device adapted to be implanted at least partially into the body of a patient

2. Discussion of the Background Art

Worldwide, 1.5 million people suffer from kidney diseases and need a kidney replacement therapy. This number will increase at a yearly rate of 6%. Innovative technologies and the individualization of treatment methods can decisively improve the quality of life for patients suffering from kidney diseases. Particular attention is given to the adaptation of the treatment to the individual basic physiological conditions of the patients.

Presently, dialysis can only incompletely replace the function of kidneys. Various parties work on improving detoxification by dialysis. In the present state of the art, a detoxification by three dialysis sessions a week, taking 4-5 hours each, means a very high physical stress and a very high time expenditure to the patient. Owing to the short and intensive dialysis periods, the cell tissue of the patient is exposed to high stress (plasmolysis), which can have an additional adverse effect on the physical condition of the patient (multimorbidity). Toxic substances accumulate over decades of dialysis so that a plurality of medical problems can occur such as, for example, cardiac insufficiency, nervous disorders, bone pain.

The principle of dialysis can be implemented in two ways. The first method is based on the principle of the osmotic effect. In this case, an appropriate membrane is used that has a suitable pore size to remove waste products between a dialysate and the blood. However, in order to achieve an appropriate effect in a minimum of time, this method already frequently used requires very large surfaces. With conventional dialysis apparatuses, this problem is solved, for example, by the use of a plurality of membrane tubes with minute diameters. However, dialysis periods of several hours are still necessary in this case, and this several times a week. Another problem of prior art is the recurrently necessary puncturing of veins and arteries with needles in order to allow the connection of the apparatus.

The object to be achieved with the disclosure is to provide an artificial kidney that is simple, resource-saving and well tolerated by the patient. It is intended to provide a system that a patient can permanently carry on or in his body without being subjected to substantial restrictions of his mobility and the quality of life.

SUMMARY

The disclosure relates to a portable device for dialysis which can be configured to be partially or completely implantable. In an embodiment of the disclosure, the device is formed by a blood chamber and a dialysis chamber which are connected through a suitable filter, and by a housing, an electro-hydraulic pump device, as well as a reservoir.

Using a suitable liquid and a hydraulic pump device, the blood chamber is compressed and blood plasma containing metabolic waste products is removed from the blood circulation. The dialysate is stored in an extracorporeal or even implantable reservoir and is diluted there so that is also possible to supply liquid to the body via the membrane and through the pumping process.

DETAILED DESCRIPTION OF THE PREFERRED EMBODIMENT

Figure 1:
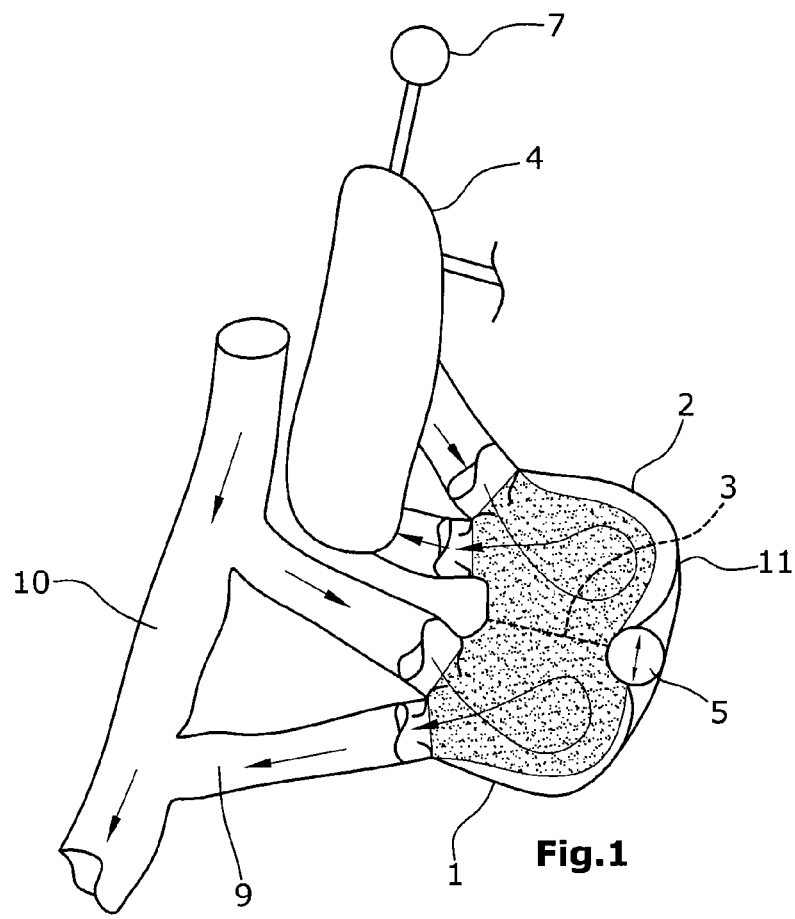
FIG. 1 is a perspective view of a portable dialysis device according to the present disclosure.

The disclosure relates to a portable apparatus for washing blood (dialysis) that may be configured to be partially or completely implantable (FIG. 1). Blood is cleaned by means of a blood chamber 1, through which blood flows, and a dialysate chamber 2, the chambers being connected by a membrane 3. Here, the osmotic effect between the blood-carrying side of the chamber and the dialysate side is used to draw waste substances from the blood chamber through the membrane. Further, purposeful pumping or drawing by means of a pump allows the separation of blood plasma or to recycle a blood substitute liquid. The pore size of the membrane advantageously is of a magnitude that allows the passage of metabolic waste products, while substantially preventing the transport of protein. The blood chamber is installed in a solid or partially solid housing 11 into which the hydraulic fluid is pumped. By actively pumping the dialysate, a defined pressure and vacuum can be exerted on the membrane 3. Thereby, it can be compressed in a purposeful manner and the blood volume of the blood chamber can thus be expelled. The hydraulic fluid compresses the chambers such that a pump effect is obtained and the chambers are flown through in an advantageous manner so that no stagnation of blood flow occurs, whereby the risk of the formation of thrombi is minimized. For avoiding return flow, the chambers are each provided with valves. Due to the optimized through-flow, the exchange effect of the membrane is further enhanced and the efficiency of the blood cleaning is increased. Owing to the continuous "24/7" (around the clock) operation of the apparatus, it is possible to provide a continuous and careful cleaning of the blood. Advantageously, the blood chamber is connected to a blood-carrying vessel, such as the aorta 10, but it may also be connected to the venous system. For this purpose, conventional vessel prostheses 9 may be used. The hydraulic fluid can be conveyed using a suitable pump 5.

The device is connected to a reservoir 4 that stores the dialysate. The device and the reservoir may be designed to be implantable. If both components are implantable, a percutaneous line or a conventional port 7 is provided for the purpose of refilling the reservoir. Owing to the use of a separate chamber for the dialysate, which is compressed by means of an electro-hydraulic drive and hydraulic fluid, an efficient mixing of the dialysate and thus an efficient dilution is obtained. Further, the use of electro-hydraulic drives ensures a controlled filling and emptying of the blood chamber, whereby an efficient purging is guaranteed. In the reservoir, the mixing causes a decrease in the concentration of metabolic waste products so that these substances will return into the circulation only to a very limited extent during a next pumping process. This is possible as long as the saturation does not exceed a threshold value. Otherwise, the liquid in the reservoir must either be cleaned or replaced using appropriate methods.

Figure 2:
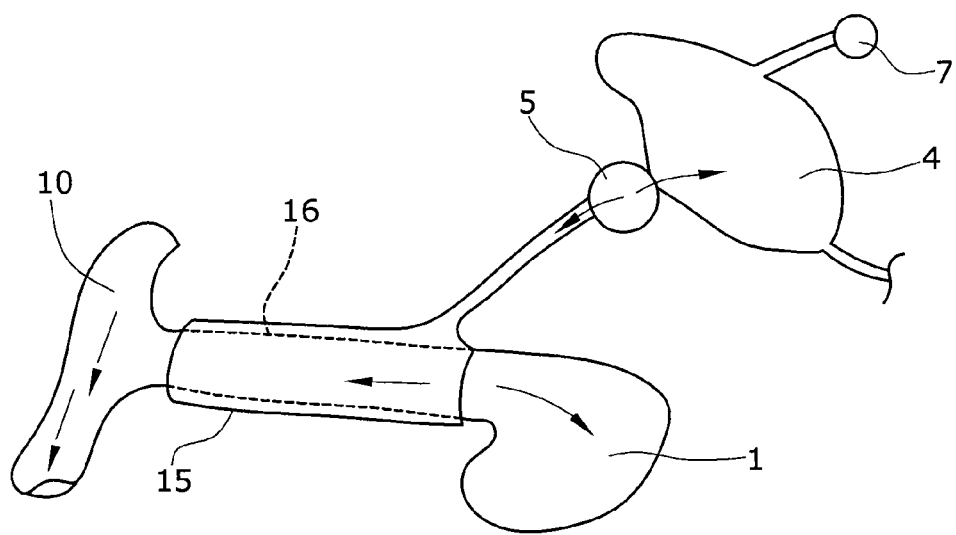
FIG. 2 is another embodiment according to the present disclosure, wherein a tubular inlet and an outlet of the pump are formed as a membrane, and enclosed another tube member that holds the dialysate.

Using suitable membrane technology, this method can also be implemented with an alternative assembly. An exemplary embodiment is illustrated in FIG. 2. A preferably tubular inlet 16 and also the outlet of the pump are formed as a membrane, respectively, and are enclosed by a larger tube member 15 that holds the dialysate. Here, it is possible to use a membrane having the same permeability in both directions, in which case the waste products have to be appropriately filtered from or bound in the dialysate so that they will not return into the blood vessel. Advantageously, the dissolved waste products can be chemically bound to larger particles which are then held back by the membrane.

As an alternative, the membrane or the surface thereof may be designed with regard to its charge or surface structure such that waste substances are repelled and thus do not return into the blood vessel.

What is claimed is:

1. A dialysis device adapted to be implanted at least partially into the body of a patient and configured for intracorporal treatment, comprising: a blood chamber, through which the patient's blood can flow; a dialysis chamber for receiving a dialysate; and a hydraulic pump device configured to compress the two chambers alternately by means of a hydraulic fluid,
   wherein both chambers are each equipped with two valves for controlling the inflow and outflow of blood and dialysate, respectively,
   and wherein both chambers are connected to each other in an area designed as a membrane.

2. The dialysis device of claim 1, wherein the hydraulic pump device generates pressure and vacuum across the membrane to remove blood plasma and metabolic waste products from the blood circulation of a patient and/or to supply liquid into the blood circulation.

3. The dialysis device of claim 1, comprising a reservoir for a liquid suitable for washing blood, the reservoir either being external with regard to the patient or being implantable into the patient.

4. The dialysis device of claim 1, wherein the reservoir comprises a port for the filling of the reservoir.

5. The dialysis device of claim 1, comprising an inlet and an outlet at the blood chamber and the dialysate chamber, respectively, each comprising a valve.

6. The dialysis device of claim 1, adapted to be implanted at least partially into the body of a patient, wherein the dialysis device comprises an implantable reservoir adapted to be filled through a percutaneous line or a port.

7. The dialysis device of claim 1, adapted to be implanted at least partially into the body of a patient, wherein said blood chamber is substantially round or ventricle-shaped.

8. The dialysis device of claim 1, adapted to be implanted at least partially into the body of a patient, wherein the dialysis device is designed to discharge used dialysate to the ureter of the patient.

* * * * *